US00PP24788P2

(12) United States Plant Patent
Hurd

(10) Patent No.: US PP24,788 P2
(45) Date of Patent: Aug. 19, 2014

(54) ***NEPETA* PLANT NAMED 'PURRSIAN BLUE'**

(50) Latin Name: *Nepeta×faassenii*
Varietal Denomination: Purrsian Blue

(71) Applicant: Kevin A. Hurd, Merrillville, IN (US)

(72) Inventor: Kevin A. Hurd, Merrillville, IN (US)

(73) Assignee: Walters Gardens Inc., Zeeland, MI (US)

( * ) Notice: Subject to any disclaimer, the term of this patent is extended or adjusted under 35 U.S.C. 154(b) by 27 days.

(21) Appl. No.: 13/815,845

(22) Filed: Mar. 16, 2013

(51) Int. Cl.
*A01H 5/00* (2006.01)

(52) U.S. Cl.
USPC ..... Plt./263.1

(58) Field of Classification Search
USPC ..... Plt./263, 263.1
See application file for complete search history.

(56) References Cited

U.S. PATENT DOCUMENTS

PP22,334 P3 * 12/2011 Egger ..... Plt./263.1

OTHER PUBLICATIONS

Perennial Resource (retrieved from the internet at <http://www.perennialresource.com/encyclopedia/view/?plant=2340> on Aug. 27, 2013, 2 pages.*
Martin, Susan M., Walters Gardens, Inc. Wholesale Catalog, Jun. 20, 2013, Summer 2013—Spring 2014, front cover, Walters Gardens, Inc., Zeeland, Michigan, USA.
Martin, Susan M., Walters Gardens, Inc. Wholesale Catalog, Jun. 20, 2013, Summer 2013—Spring 2014, p. 157, Walters Gardens, Inc., Zeeland, Michigan, USA.

* cited by examiner

*Primary Examiner* — June Hwu
*Assistant Examiner* — Keith Robinson

(57) ABSTRACT

The new and distinct hardy perennial plant, *Nepeta* 'Purssian Blue', has rounded, short and compact habit with mostly upright stems. The foliage is small and serrate with slightly rounded teeth. Flowers are a periwinkle blue with persistent dark-purple to magenta-purple calyces.

1 Drawing Sheet

Botanical denomination: *Nepeta×faassenii.*
Variety designation: 'Purrsian Blue'.

BACKGROUND OF THE INVENTION

The present invention relates to a new and distinct cultivar of *Nepeta* named 'Purrsian Blue'. The new plant resulted from a cross between Nepeta 'Six Hills Giant' (not patented) (female or seed parent) and an unknown selection named only as 'Eldean' (non-patented) (male or pollen parent) hybridized by Kevin A. Hurd in the summer of 2009, seed harvested Oct. 26, 2009 and originally given the breeder code K0-19-01. 'Purrsian Blue' was approved in a final evaluation in the summer of 2011 and slated for later introduction. The new plant was selected based on the long blooming and compact traits. The new plant has been asexually propagated in a nursery in Zeeland, Mich. by tip cuttings with the resultant plants remaining identical to the original plant, stable and true to type in successive generations.

SUMMARY OF THE INVENTION

*Nepeta* 'Purssian Blue' is different from its parents and all other Catmint known to the inventor. In comparison to the female parent, *Nepeta* 'Six Hills Giant', the new plant is considerably shorter and more compact. Compared to the male parent, 'Eldean', the new plant is also shorter and more compact. The nearest comparison variety is *Nepeta* 'Novanepjun' U.S. Plant Pat. No. 23,074 more commonly known as 'Junior Walker'. 'Purrsian Blue' is shorter and more rounded in habit than 'Junior Walker'. The new plant, in comparison to *Nepeta* 'Psfike' U.S. Plant Pat. No. 18,904 is more upright, less decumbent, more compact in habit and the foliage of the new plant is serrate with slightly rounded teeth as opposed to the crenate foliage of 'Psfike'. In comparison to 'Purple Haze' U.S. Plant Pat. No. 23,180 the new plant is shorter and more compact and lighter or less purple in flower. 'Purrsian Blue' is significantly smaller in height and width in comparison to 'Blue Dragon' U.S. Plant Pat. No. 22,334. In comparison to *Nepeta* 'Cars Meow' (co-pending application) the present plant is more rounded and shorter in habit and has more rounded serration of the foliage and periwinkle blue flower compared to sky-blue flower of 'Cat's Meow'. The present invention has not been evaluated under all possible environmental conditions. The phenotype may vary with changes in the environment such as light, temperature, water and nutrient availability, etc. without a change in the genotype of the plant. *Nepeta* 'Purrsian Blue' is unique from all other Catmint known to the inventor in the following combined traits:

1. The habit is rounded, short and compact with mostly upright stems.
2. Foliage is small and serrate with slightly rounded teeth.
3. Flowers are periwinkle blue and persistent dark-purple to magenta-purple calyces.

BRIEF DESCRIPTION OF THE DRAWINGS

The photographs of the new plant *Nepeta* 'Purrsian Blue' are of a two-year old plant in a full sun display garden in Zeeland, Mich. and demonstrate the unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
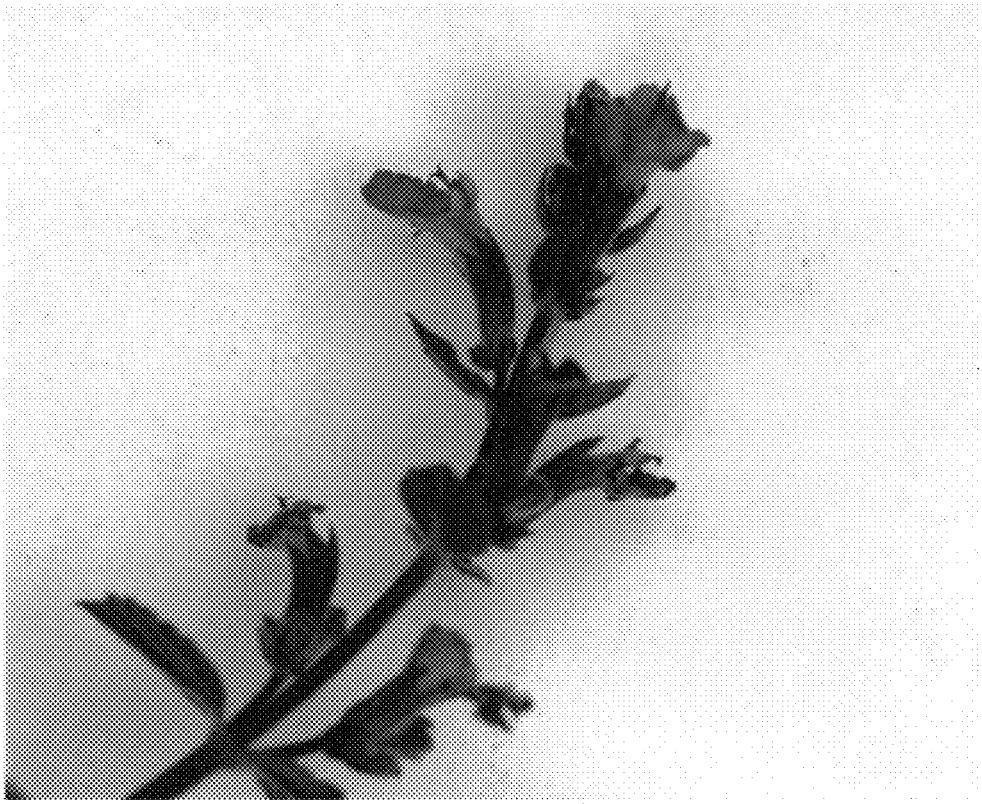
FIG. 1 shows a close-up of the flower.
Figure 2:
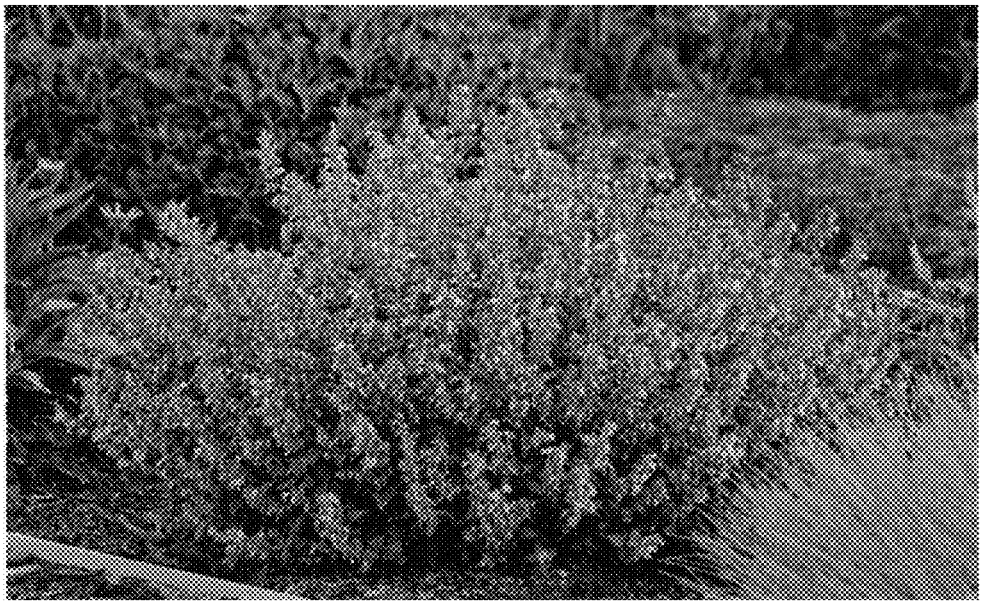
FIG. 2 shows the overall habit of *Nepeta* 'Purrsian Blue'.

The following descriptions are based on a two-year old plant of *Nepeta* 'Purrsian Blue' grown in a full-sun display garden in sandy loam with supplemental water and fertilizer as needed. The color references are based on the 2001 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: 'Six Hills Giant' (female, seed), 'Eldean' (male, pollen).

Plant habit: Herbaceous perennial; upright mounding to about 32 cm tall and 45 cm wide at the base in flower.

Growth: Rapid; finishing in a standard #1-15 cm container in about 12 to 15 weeks from rooted plug; time to initiate roots at 23° C. about one week.

Root: Fine, freely branching; color nearest RHS 158D depending on soil type and nutrient content.

Foliage: Opposite, simple, ovate; rugose on both abaxial and adaxial surfaces; margins serrate with slightly rounded teeth; pubescent on abaxial and adaxial surfaces; apex acute; base rounded; blade size about 12.0 mm long and 6.0 mm wide.

Venation: Longitudinal; impressed on adaxial surface and ribbed on abaxial surface.

Vein color: Nearest RHS 137C on adaxial surface and nearest RHS 138C on abaxial surface.

Leaf color: Adaxial surface nearest RHS N138B, abaxial surface between RHS N138C and RHS 138D.

Petiole: Pubescent adaxial and abaxial; about 4.0 mm long and 2.0 mm diameter in basal region of stem becoming sessile in distal region.

Petiole color: Between RHS 136C and RHS N138C with tinting in high sun exposure between RHS N186B and RHS N186C.

Stem: Pubescent, quadangular, about 6.0 mm across at base and 3.0 mm at just below lowest flowers; internodes average about 2.4 cm apart with greatest distance in the middle of the stem; about 13 nodes per stem.

Stem color: Between RHS 136C and RHS N138C with tinting in high sun exposure between RHS N186B and RHS N186C; node color normally same as surrounding stem.

Inflorescence: Cymosely clustered with many flowers either sessile or branched at verticillasters in the upper nodes; about 9 to 33 flowers per node and about 120 per inflorescence stem or peduncle.

Peduncle: Main stem mostly vertical to about 32 cm tall with flowers on the distal 16 cm.

Pedicel: Sessile.

Flower bud: Curved clavate; about 9.0 mm long and 4.5 mm wide at the widest point one day prior to opening; adaxial surface pubescent.

Flower bud color: Petal portion nearest RHS 96D, calyx portion nearest RHS N138A with tinting of between RHS N186D and RHS 187B.

Flowers: Zygomophic, bilabiate, sympetalous with basal 8.0 to 9.0 mm fused; bisexual or lacking androecium; synsepalous.

*Upper lip*.—Pubescent on abaxial surface, glabrous on adaxial surface; with three lobes, dorsally flattened perpendicularly to flower axis, about 13.0 mm long, vertical top lobe rounded with emarginated apex, top lobe about 6.0 mm across at widest portion; two horizontal side lobes flaring at about 90 degrees from top lobe, horizontal side lobes are rounded with rounded apices, side lobes about 1.2 mm across and long; adaxial color between RHS 94D and RHS 97A; abaxial color nearest RHS 97A.

*Lower lip*.—Consisting of two fused lobes, dorsally flattened to perpendicular to flower axis; pubescent on abaxial and center outside section of adaxial surfaces; apex crenate with five rounded teeth, base fused; adaxial color nearest RHS 100C with dark spots about 0.5 mm diameter and less in tube throat nearest RHS 99A; abaxial color nearest RHS 97A.

*Calyx*.—Synsepalous, 5-merous fused into sepal tube in basal 6.0 mm and separated in distal 1.0 mm; acute apex, base fused; with about 15 conspicuous ribs; pubescent adaxial, glabrous abaxial; persistent; about 7.0 mm long and 2.0 mm diameter, adaxial color in high direct light between RHS 70C and RHS 70D with darker ribs of RHS 79C and in less light base color of RHS N138A with ribs and tinting of RHS N186C; abaxial color nearest RHS N144D at base and tinting of nearest RHS N186C increasing with more direct sun.

*Gynoecium*.—Single compound ovary with two carpels, single gynobasic style, and stigma split in two parts; style about 9.0 mm long and 1.0 mm diameter, style color nearest RHS N89D; stigma split in last 2.0 mm to sharply acute apex, stigma color nearest RHS 83B; ovary four-lobed, each lobe ovoid, about 1.0 mm long and 0.5 mm across, ovary color between RHS 145A and RHS N144D.

*Androecium*.—Anthers, filaments and pollen not observed under some conditions or only two stamens that are adnate to the inner corolla tube; when present anthers not developed, no pollen observed; filaments when present about 1.0 mm long and less than 0.5 mm diameter; filament color whiter than RHS 155D; stamen when present ovoid, about 1.0 mm long and 0.5 mm diameter, stamen color between RHS N187B and RHS 187A.

Flowering period: June into October in West Michigan; individual flowers remain open for up to three days.

Fragrance: Foliage and stem herbal almost minty fragrance; no fragrance detected given off by flowers.

Fruit and seed: Rare, nutlets, flattened, round; about 1.5 mm diameter and 0.5 mm thick; nearest RHS 200B.

Pest and disease susceptibility: No resistance beyond that which is typical for *Nepeta* but typically not prone to browsing by deer or rodents.

The invention claimed is:

1. The new and distinct hardy perennial plant, *Nepeta* 'Purssian Blue' essentially as herein described and photographed useful for landscaping as a specimen, en masse, or in a container to bring color and fragrance to a garden and attract butterflies and hummingbirds.

* * * * *